United States Patent [19]

De Giacomi

[11] Patent Number: 5,781,933
[45] Date of Patent: Jul. 21, 1998

[54] AERODYNAMIC PEAKED CAP

[75] Inventor: Giancarlo De Giacomi, Segrate Milano, Italy

[73] Assignee: General Building s.a.s. di De Giacomi Giancarlo, Segrate Milano, Italy

[21] Appl. No.: 670,437

[22] Filed: Jun. 26, 1996

[30] Foreign Application Priority Data

Jun. 30, 1995 [IT] Italy .................... MI950460 U

[51] Int. Cl.⁶ ............................................. A42B 1/06
[52] U.S. Cl. ............................................. 2/195.1; 2/195.6
[58] Field of Search ................... 2/7, 171.2, 171.4, 2/171.5, 171.6, 171.7, 172, 175.1, 175.3, 175.5, 175.6, 195.1, 195.6, DIG. 1

[56] References Cited

U.S. PATENT DOCUMENTS 1,486,102  3/1924  Merton .................... 2/171.4
4,292,689  10/1981 Townsend, Jr. .
5,091,995  3/1992  Oates .

*Primary Examiner*—Diana Biefeld
*Attorney, Agent, or Firm*—Browdy and Neimark

[57] ABSTRACT

The aereodynamic peaked cap is constructed with a crown, as a turned upside down bowl to cover the wearer's head and an outwardly projecting visor. The visor comprises: a) a middle frame with one or more apertures inside. b) a mesh cover below,which air coming from below, can pass through. c) an upper streamlined sloping cloth connected to the crown by buttons.Between the crown and the upper cloth there are some apertures as ducts for air flow coming from below the visor. By buttoning the buttons male on the upper cloth and the buttons female on the crown in a different alternate way the formed folds as air ducts can be moved from the center to the sides of the visor, so that, in case of rain and snow, to avoid vertical penetration of rain into the middle duct, this duct can be closed and the side ones can be enlarged, to allow however a greater air flow. Advantages: regulation of resistance to wind currents of the visored cap is possible, according to wind and user's speed to avoid unintenional removal from the wearer's head.

6 Claims, 3 Drawing Sheets

FIG.1(a)
FIG.1(b)
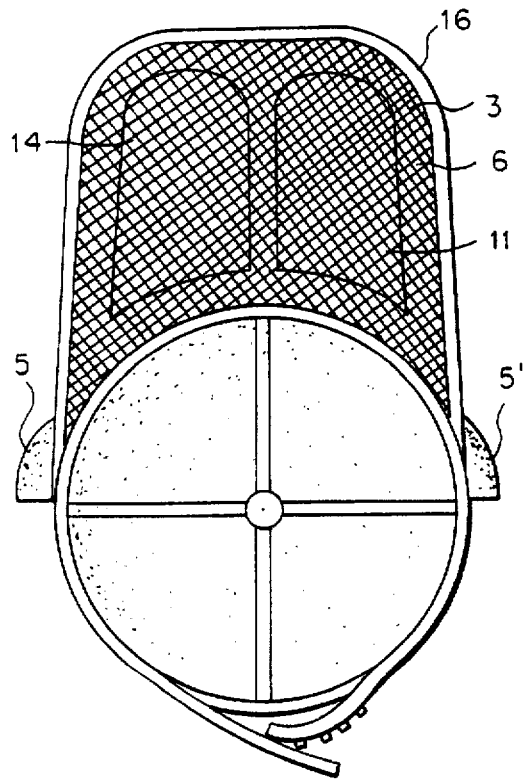
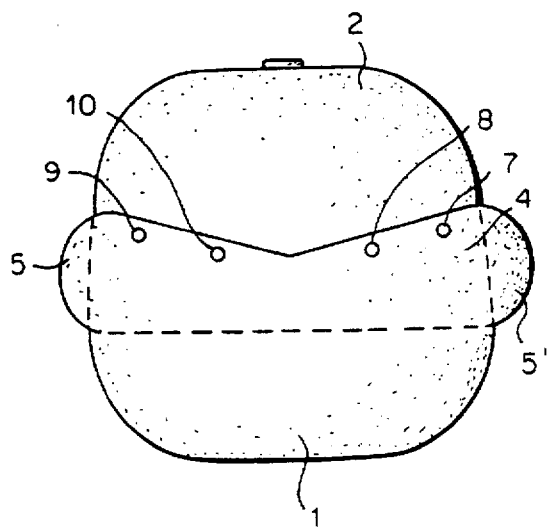
FIG.1(c)
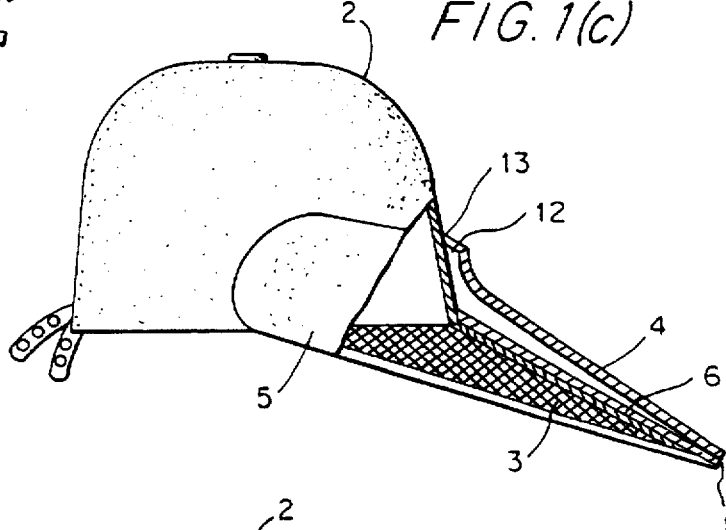
FIG.1(d)
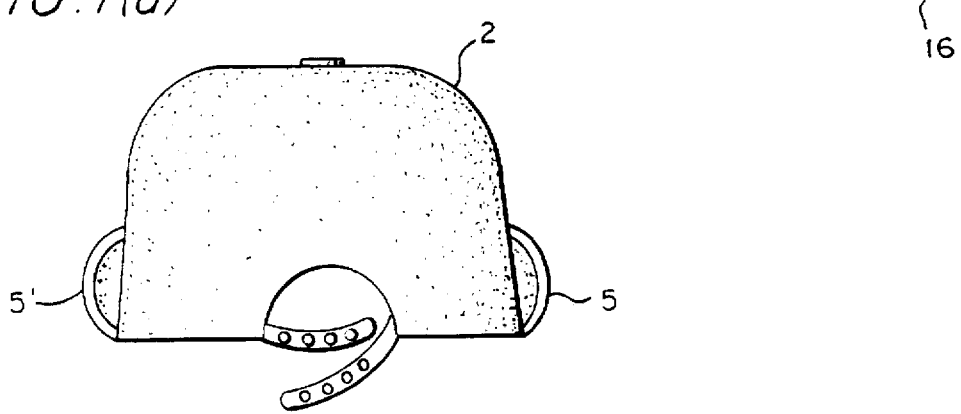

AERODYNAMIC PEAKED CAP

TECHNICAL FIELD

The present invention relates to peaked caps worn usually by sportpeople to protect against sunrays, rain and snow, or to gather up long hair into a hat in case of wind, as for instance when riding a bicycle, a motorcycle, skying, running, jogging, driving a cabriolet, and so on.

BACKGROUND ART

Up to now peaked caps on the market have great problem of aereodynamics because the visor has high resistance to wind currents, proportional to its surface extending from the crown, as a turned upside down bowl,so that in case of wind,or when the user is running or moving speedily, it usually happens that the wearers may lose their caps, blown away by the wind. The reason for the above trouble, is that air blows against the wearer's front and the visor, and having no way of escape and passage through this obstacle, it applies pressure to the visor and blows the cap away.

Moreover the shape of the usual peaked caps is not aereodynamic at all. In fact, considering the cap made of two parts, the crown, as a turned upside down bowl, that is slipped on the wearer's head, land the visor, as protection against sun rays, rain and snow, the shape of usual caps on the market as not aereodynamic because the front and upper part of the hat crown, from the top to the joint line with the visor, has a very high slope (about 70°–80°) so that it is like a high barrier to wind, with a high $C_x$ index against wind currents. Because of the above reason, some users like better to turn the hat and wear it with the visor on the back.

DISCLOSURE OF INVENTION

It is therefore an object of present invention to supply means particularly useful to reduce the resistance to wind of the visored cap and make it more aereodynamic and firm on the user's head.

According to a preferred embodiment of the present invention, the peaked cap comprises: 1) a crown, as a turned upside down bowl, that covers the wearer's head; 2) the visor that includes a) a frame in the middle, made from plastic, wood or a metal such as iron, etc, with one or more apertures of different shapes inside, b) a mesh cover below, which air can pass through, for aesthetic and manufacturing reasons, c) an upper streamlined cloth with a suitable slope to prevent penetration of direct sun rays to the user's eyes. Another purpose of this upper streamlined cloth is to protect the user's eyes and face against rain and snow in case of bad weather. This streamlined cloth is stretched with a suitable slope over the middle frame between the front side of the peripheral rounded edge of the visor, where it is sewn, up to the front part of the crown. The connection between the upper cloth and the front part of the crown is achieved by buttons, so that by fastening and joining in different ways and positions the female buttons e.g. button holes on the crown and the male ones on the upper cloth of the visor, some folds are formed, that become the ducts for air passage and can be moved from the center to the sides, according to the weather condition and user's movement speed. In case of rain or snow falling down, air ducts in the center must be closed, to avoid water and snow penetration, on the contrary the side apertures must be left opened, where rain can't enter. In case an elastic fabric is used for the upper sheath, a better adherence is got between the crown and the upper cloth of the visor, to close the air ducts in the middle in a better way. So, by fastening male and female buttons in different ways, the for med folds become ducts for wind passage, larger or stricter, to reduce or to increase resistance to air flow through, according to wind or user's speed. As above explained, in comparison with standard caps on the market, three main improvements have been carried out: 1) less resistance to wind current, owing to the fact that visor is not a solid obstacle to wind, but a mesh which the wind current can pass through. 2) this cap is more streamlined than usual ones, owing to the shape of visor with an upper suitable slope and a consequent less high front of the crown. 3) it has been added the possibility of reducing the resistance to wind current more or less at will, according to the user's and wind speed.

Owing to this shape of the-visor, the air, after having entered the mesh below, blows against the lowest band of the crown, so that this pressure of the crown on the user's forehead increases the firmness of the cap on the user's head.

The best improvement in comparison with the standard caps, is evident when the user raises his head over the horizontal line, for instance of about 45 degrees, so that obviously the visor too slopes over the horizontal line of the same degrees, because in this case the resistance to wind of usual caps increases much more than he ones of this invention and the removal of standard cap from the user's head happens at a much lower speed than the one of this invention, as really tested. Instead of buttons, two bands can be used, the male ones with little plastic hooks on the crown, and the female pile one (named "hook and loop fasteners" and available under the trademark VELCRO) on the upper cloth of visor, so that being the former shorter than the latter some folds are formed, as ducts for air passage.

If the middle frame of the visor is strong enough to avoid creases and folding, leaving aesthetics out of consideration, visor reinforcement with mesh can be unnecessary, so that a visor is used with one or more apertures in the middle frame, completely open, even if in this case manufacturing is more difficult owing to difficulty of sewing the upper cloth to the middle frame and a cloth cover around the rims of the apertures.

Further characteristics and advantages of the present invention will better emerge from the detailed description that follows of an embodiment of the invention, illustrated in the form of a non limiting example in the enclosed drawings in which:

FIG. 1(a) is a bottom plan view of a first embodiment according to the present invention;

FIG. 1(b) is a front elevational view thereof;

FIG. 1(c) is a side elevational view thereof, partly in section;

FIG. 1(d) is a rear elevational view thereof;

Figure 2A:
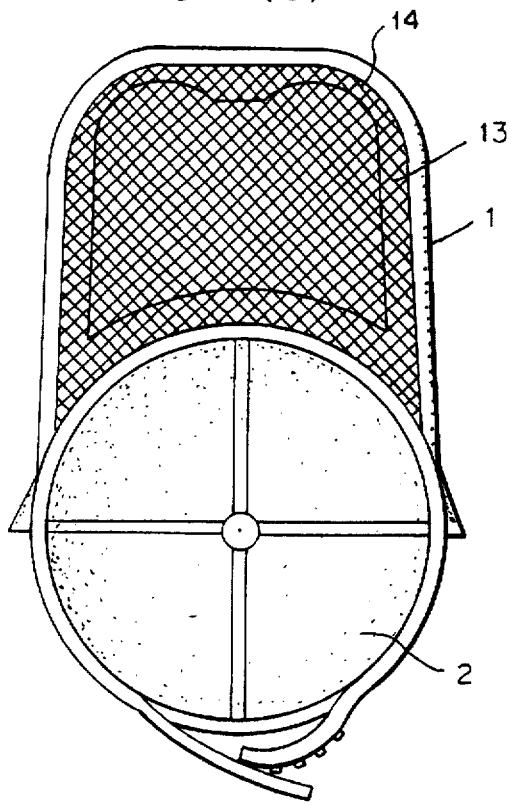
FIG. 2(a) is a bottom plan view of a second embodiment according to the present invention.

Referring to FIGS. 1(a) to 1(d) a particular embodiment of a visored cap is shown made of two main parts: the visor 1 with two apertures 11 and 14 and the crown 2 that has to cover the user's head in FIGS. 1(a). The view from below as per FIG. 1(a) shows the visor that comprises the middle frame 6 connected inside to the mesh 3. The partially sectioned side elevational view FIG. 1(c) shows the mesh 3 and the upper and streamlined cloth 4 that can be rigid or soft, which is stretched between the visor rounded edge 16 and the front part of the crown 2: the connection between the former and the latter, is achieved by the buttons 7-8-9-10 shown in view FIG. 1(b) so that by unbuttoning these, air ducts become larger for drag reducing, and by fastening and joining these buttons in an alternate way, central folds as air ducts become larger or more restricted and air canalizers move from the center to the sides 5 and 5'. Wind currents, coming from below the mesh, enter the mesh 3, blow against the lower band of the crown 13, increasing the pressure on the wearer's forehead and improving the firmness of the cap on the user's head, enter the air canalizer 12 and go out through this duct in the middle of the visor 1, and through the ducts 5 and 5' on both sides.

In case it is raining or snowing, to avoid rain or snow entering the air relief passage or duct 12, this duct must be closed by joining the buttons 8 and 10 in the center, or in a better way joining the male button 8 with the female button 7 and in the same way the male button 10 on the upper cloth 4 with the female button 9 on the crown, so that in the center the upper cloth 4 is stretched and connected without ducts to the front part of the crown 2, and the side ducts 5 and 5', increase their width and consequent the air flow through.

Figure 2B:
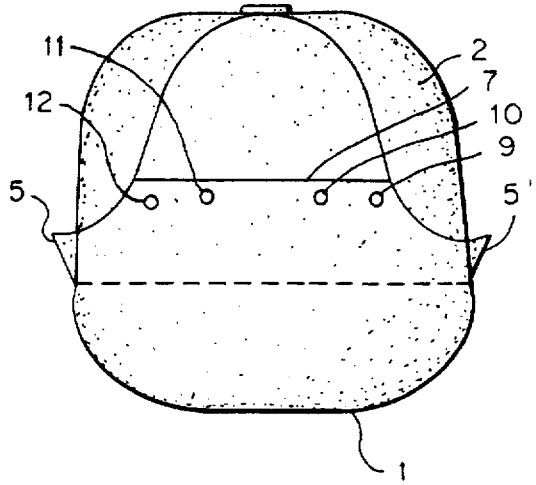
FIG. 2(b) is front elevational view thereof.
Figure 2C:
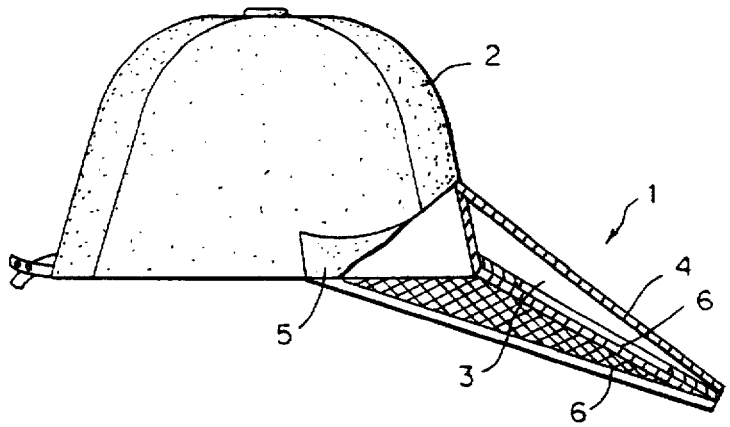
FIG. 2(c) is a side elevational view thereof, partly in sections.
Figure 2D:
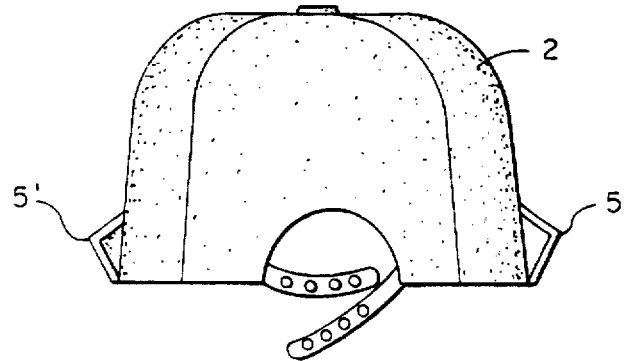
FIG. 2(d) is a rear elevational view thereof.
Figure 3A:
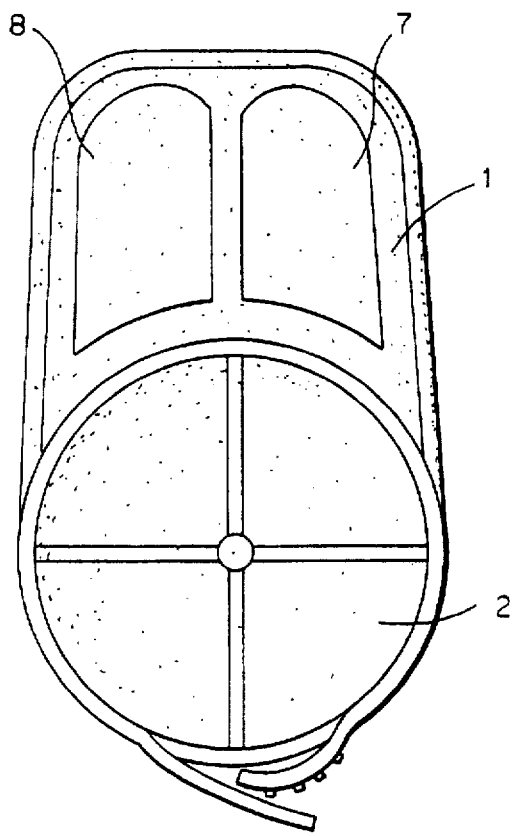
FIG. 3(a) is a bottom plan view of a third embodiment according to the present invention.
Figure 3B:
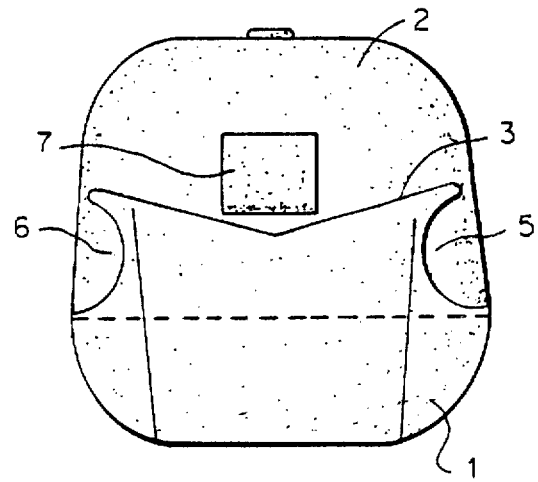
FIG. 3(b) is a front elevational view thereof.
Figure 3C:
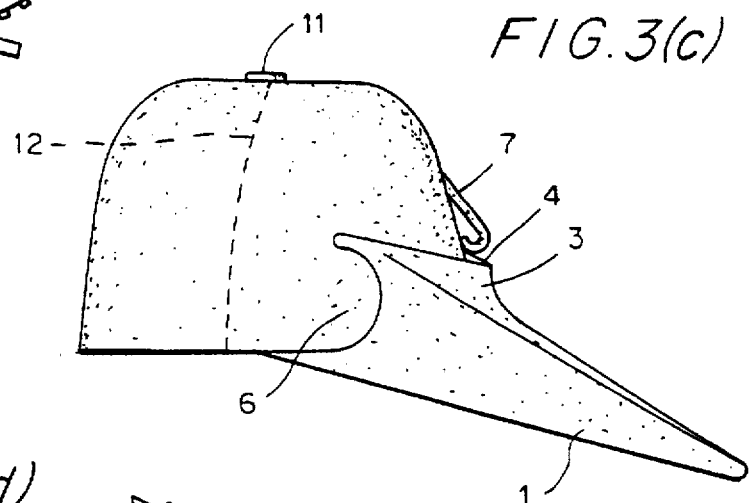
FIG. 3(c) is a side elevational view thereof.
Figure 3D:
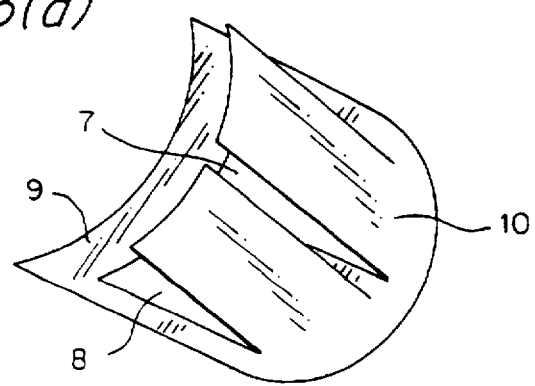
FIG. 3(d) is a perspective view of a part thereof.

Referring to FIGS. 2(a) through 2(d), another embodiment of a different cap according to this invention, which comprises a visor 1 and the crown 2 shown in view FIG. 2(b). The shape of cap changes in comparison with the first one shown in FIG. 1, mainly in the front view, where upper sloping cloth 4 in the view (c) has a different outline 7 shown in the view (b). In this embodiment the buttons 9-10-11-12 are applied only for aesthetic purposes, because the upper cloth 4 in the view of FIG. 2 is stretched over the middle frame 6 and the mesh 3, as a streamlined air conveyer, but completely sewn to the cap crown in the center, without central air ducts, that are located only on both sides 5 and 5'. The middle frame 13 has only one aperture 14. Referring to FIGS. 3(a) through 3(d) another embodiment of a different shape of visored cap is shown, where the visor 1 has two large apertures inside 7 and 8 and no mesh cover below, used in other models, as reinforcement and improvement of aesthetics. The streamlined upper cloth 3 as seen in FIG. 3(c) has no buttons but being of rigid fabric, has an unchanging air duct in the middle 4 and two side ducts 5 and 6 as seen in FIG. 3(b) and 3(c).

The view of FIG 3. (d) shows a particular shape of middle frame 9, where the apertures 7 and 8 have upper sloping tabs 10 as support of the upper streamlined cloth 3 to keep it stretched if the cloth 3 is of soft fabric and always lifted from the frame, to allow a continuous air flow through the apertures.

To avoid the falling down of rain and snow into middle air duct 4, a folded band 7 is sewn over this duct 4 to be spread for vertical duct closing, in case of rain and snow.

The side ducts 5 and 6 are rounded shaped to get larger apertures and a consequent greater air flow, with less extension in width on both sides of the cap.

I claim:

1. A visored cap comprising a crown corresponding to the general shape of a turned upside-down bowl for fitting over an upper portion of a wearer's head; and a visor having a peripheral edge extending outwardly from said crown, said visor comprising a relatively rigid frame having at least one large aperture extending therethrough, a mesh covering extending below said frame, said mesh covering being sufficiently porous to permit wind to pass therethrough, and an upper streamlined sloping cloth stretched between said peripheral edge of said visor and a front part of said crown, with said frame and said sloping cloth defining an air passageway therebetween, and an upper portion of said cloth being connected to said front part of said crown with at least one air passage between said sloping cloth and said front part of said crown.

2. A visored cap according to claim 1 comprising a series of buttons for releasably connecting said upper cloth to said front part of said crown.

3. A visored cap according to claim 1 comprising at least one hook and loop fastener for releasably connecting said upper cloth to said front part of said crown.

4. A visored cap according to claim 1 wherein said frame has at least two apertures extending therethrough.

5. A visored cap according to claim 1 having at least two air relief passages between said front part of said crown and an upper edge of said upper cloth.

6. A visored cap according to claim 1 wherein said upper cloth is connected to the front part of the crown in such a way as to provide large side ducts of rounded shape at opposite lateral sides of said visor.

* * * * *